(12) United States Patent
Alemana et al.

(10) Patent No.: US 12,324,567 B2
(45) Date of Patent: Jun. 10, 2025

(54) APPARATUS AND METHOD FOR CLEANING A MEDICAL DEVICE

(71) Applicant: SABAN VENTURES PTY LIMITED, Alexandria (AU)

(72) Inventors: Gilbert T. Alemana, Lane Cove West (AU); Mathias Berg-Johansen, Lane Cove West (AU); Gavin Spargo, Lane Cove West (AU); Panagiotis Thrasou, Lane Cove West (AU); Madeleine Jane Clegg, Lane Cove West (AU); David Anthony Pidcock, Lane Cove West (AU); Mark Lewis Holloway, Lane Cove West (AU); Forough Khandan, Lane Cove West (AU); Mohsen Nabipoor, Lane Cove West (AU); Alexander Galkin, Lane Cove West (AU)

(73) Assignee: Saban Ventures Pty Limited, Macquarie Park (AU)

( * ) Notice: Subject to any disclaimer, the term of this patent is extended or adjusted under 35 U.S.C. 154(b) by 982 days.

(21) Appl. No.: 17/285,892

(22) PCT Filed: Oct. 16, 2019

(86) PCT No.: PCT/AU2019/051127
§ 371 (c)(1),
(2) Date: Apr. 15, 2021

(87) PCT Pub. No.: WO2020/077406
PCT Pub. Date: Apr. 23, 2020

(65) Prior Publication Data
US 2021/0338070 A1    Nov. 4, 2021

(30) Foreign Application Priority Data

Oct. 16, 2018  (AU) ................................ 2018903910
Jul. 31, 2019  (AU) ................................ 2019902732

(51) Int. Cl.
| | | |
|---|---|---|
| A61B 1/12 | (2006.01) | |
| A61B 90/70 | (2016.01) | |
| A61B 90/96 | (2016.01) | |

(52) U.S. Cl.
CPC .............. *A61B 1/123* (2013.01); *A61B 1/125* (2013.01); *A61B 90/70* (2016.02); *A61B 90/96* (2016.02);
(Continued)

(58) Field of Classification Search
None
See application file for complete search history.

(56) References Cited

U.S. PATENT DOCUMENTS 8,226,774 B2   7/2012  Labib et al.
8,967,168 B1 *  3/2015  Gusanders ............... A61L 2/18
                                                        4/619
(Continued)

FOREIGN PATENT DOCUMENTS

EP   2060276 B1   4/2012
EP   3246049 A2  11/2017
(Continued)

OTHER PUBLICATIONS

International Search Report, PCT/AU2019/051127, dated Dec. 17, 2019, 4 pages.
(Continued)

*Primary Examiner* — Rita P Adhlakha
(74) *Attorney, Agent, or Firm* — Edell, Shapiro & Finnan, LLC

(57) ABSTRACT

Described herein is a cleaning apparatus (10) for a medical device (12) having one or more internal channels. Further described is a method for cleaning the medical device using the cleaning apparatus. The cleaning apparatus includes at least two cleaning pumps (20) adapted to pump a viscoelas-
(Continued)

tic liquid (22), each cleaning pump having individual flow control. Each cleaning pump is also fluidly connectable to one or more of the internal channels to allow the viscoelastic liquid to be pumped therethrough thereby removing contaminants.

20 Claims, 10 Drawing Sheets

(52) U.S. Cl.
CPC . *A61B 2090/701* (2016.02); *A61B 2560/0462* (2013.01)

(56) References Cited

U.S. PATENT DOCUMENTS

| | | | |
|---|---|---|---|
| 10,722,491 B2* | 7/2020 | Ochoa Rodríguez ... | A61P 25/16 |
| 10,772,491 B2* | 9/2020 | Chouinard ............. | G01M 3/02 |
| 2011/0097248 A1 | 4/2011 | Tomita et al. | |
| 2012/0211033 A1 | 8/2012 | Onishi et al. | |
| 2016/0157956 A1 | 6/2016 | Aehlig | |
| 2017/0332892 A1 | 11/2017 | Yang et al. | |
| 2018/0094214 A1 | 4/2018 | Labib et al. | |

FOREIGN PATENT DOCUMENTS

| | | |
|---|---|---|
| JP | 2004049451 A | 2/2004 |
| JP | 2006-314709 A | 11/2006 |
| JP | 2012504431 A | 2/2012 |
| JP | 2012-071017 A | 4/2012 |
| JP | 2012-086014 A | 5/2012 |
| JP | 2014-161737 A | 9/2014 |
| JP | 2014-526321 A | 10/2014 |
| JP | 2016-530936 A | 10/2016 |
| JP | 2017-202330 A | 11/2017 |
| WO | 2010/010787 A1 | 1/2012 |
| WO | 2012/035982 A1 | 2/2014 |
| WO | 2014/045718 A1 | 8/2016 |
| WO | 2019113634 A1 | 6/2019 |
| WO | 2019195403 A1 | 10/2019 |

OTHER PUBLICATIONS

Written Opinion, PCT/AU2019/051127, dated Dec. 17, 2019, 7 pages.
International Preliminary Report on Patentability, dated Aug. 28, 2020, 7 pages.
Extended European Search Report in counterpart European Application No. 19873371.9-1126, mailed Jun. 29, 2022, 8 pages.
Office Action in counterpart Japanese Application No. 2021-520327, mailed May 17, 2023, 15 pages.
Communication pursuant to Article 94(3) EPC in counterpart European Application No. 19 873 371.9-1122, mailed Jun. 7, 2024, 5 pages.
Travis W Walkera et al., "Enhanced particle removal using viscoelastic fluids", Journal of Rheology, Society of Rheology, US, vol. 58, No. 1, Nov. 30, 2013 (Nov. 30, 2013), pp. 63-88, XP009527519, ISSN: 0148-6055, DOI: 10.1122/1.4832637.

* cited by examiner

APPARATUS AND METHOD FOR CLEANING A MEDICAL DEVICE

REFERENCE TO RELATED APPLICATIONS

This application is a U.S. national stage application of International Patent Application No. PCT/AU2019/051127, filed Oct. 16, 2019, which claims the benefit of Australian Patent Application No. 2019902732, filed Jul. 31, 2019, and Australian Patent Application 2018903910, filed Oct. 16, 2018, the entire disclosures of which are incorporated herein by reference.

TECHNICAL FIELD

This invention relates to an apparatus, system and method for cleaning the interior channels of medical devices, and in particular for cleaning the internal channels including lumens, cylinders, valve sockets and connectors of contaminated medical instruments. However, it will be appreciated that the invention is not limited to this particular field of use.

BACKGROUND

The following discussion of the prior art is intended to place the invention in an appropriate technical context and enable the associated advantages to be fully understood. However, any discussion of the prior art throughout the specification should not be considered as an admission that such art is widely known or forms part of the common general knowledge in the field.

An endoscope is an elongate tubular medical device that may be rigid or flexible and which incorporates an optical or video system and light source. Typically, an endoscope is configured so that one end can be inserted into the body of a patient via a surgical incision or via one of the natural openings of the body. Internal structures near the inserted end of the endoscope can thus be viewed by an external observer.

As well as being used for investigation, endoscopes are also used to carry out diagnostic and surgical procedures. Endoscopic procedures are increasingly popular as they are minimally invasive in nature and provide a better patient outcome (through reduced healing time and exposure to infection) enabling hospitals and clinics to achieve higher patient turnover.

Endoscopes typically take the form of a long tube-like structure with a 'distal tip' at one end for insertion into a patient and a 'connector end' at the other end, with a control handle at the centre of the length. The connector end is normally hooked up to a supply of light, water, suction and pressurised air. The control handle is held by the operator during the procedure to control the endoscope via valves and control wheels. The distal tip contains the camera lens, lighting, nozzle exits for air and water, exit point for suction and forceps. All endoscopes have internal channels used either for delivering air and/or water, providing suction or allowing access for forceps and other medical equipment required during the procedure. Some of these internal channels run from one end of the endoscope to the other, while others run via valve sockets at the control handle. Some channels bifurcate while and others join from two into one.

The high cost of endoscopes means they must be re-used. As a result, because of the need to avoid cross infection from one patient to the next, each endoscope must be thoroughly cleaned and disinfected or sterilised after each use. This involves the cleaning of not only the outer of the endoscope, but also cleaning and disinfecting the internal channels/lumens.

Endoscopes used for colonoscopic procedures are typically between 2.5 and 4 meters long and have one or more lumen channels of diameter of no more than a few millimetres. Ensuring that such long narrow channels are properly cleaned and disinfected between patients presents a considerable challenge. The challenge of cleaning is also made more difficult by the fact that there is not just one configuration/type of endoscope. Indeed, there are a variety of endoscopic devices, each suited to a particular insertion application i.e. colonoscopes inserted into the colon, bronchoscopes inserted into the airways and gastroscopes for investigation of the stomach. Gastroscopes, for instance, are smaller in diameter than colonoscopes; bronchoscopes are smaller again and shorter in length while duodenoscopes have a different tip design to access the bile duct.

A variety of options are available to mechanically remove biological residues from the lumen which is the first stage in the cleaning and disinfection process. By far the most common procedure for cleaning the lumens utilise small brushes mounted on long, thin, flexible lines. Brushing is the mandated means of cleaning the lumen in some countries. These brushes are fed into the lumens while the endoscope is submerged in warm water and a cleaning solution. The brushes are then pushed/pulled through the length of the lumens in an effort to scrub off the soil/bio burden. Manual back and forth scrubbing is typically required. Water and cleaning solutions are then flushed down the lumens. These flush-brush processes are repeated three times or until the endoscope reprocessing technician is satisfied that the lumen is clean. At the end of this cleaning process air is pumped down the lumens to dry them. A flexible pull-through device having wiping blades may also be used to physically remove material. A liquid flow through the lumen at limited pressure can also be used.

In general, however, only the larger suction/biopsy lumens can be cleaned by brushing or pull throughs. Air/water channels are too small for brushes so these lumens are usually only flushed with water and cleaning solution.

After mechanical cleaning, a chemical clean is carried out to remove the remaining biological contaminants. Because endoscopes are sensitive and expensive medical instruments, the biological residues cannot be treated at high temperatures or with strong chemicals. For this reason, the mechanical cleaning needs to be as thorough as possible. In many cases, the current mechanical cleaning methodologies fail to fully remove biofilm from lumens, particularly where cleaning relies on liquid flow alone. Regardless of how good the conventional cleaning processes are, it is almost inevitable that a small microbial load will remain in the channel of the lumen.

There has been significant research to show that the method of cleaning with brushes, even when performed as prescribed, does not completely remove biofilm in endoscope lumens. As well as lacking in efficacy, the current manual brushing procedures suffer from other drawbacks. The large number of different endoscope manufacturers and models results in many minor variations of the manual cleaning procedure. This has led to confusion and ultimately poor compliance in cleaning processes. The current system of brushing is also hazardous in that the chemicals that are currently used to clean endoscopes can adversely affect the reprocessing staff.

The current system of manual brushing is also labour intensive, leading to increased cost. Thus, the current approaches to cleaning and disinfecting the lumens in medical cleaning apparatus are still inadequate and residual microorganisms are now recognised as a significant threat to patients and staff exposed to these devices.

There is evidence of bacterial transmission between patients from inadequate cleaning and disinfection of internal structures of endoscopes which in turn has led to patients acquiring mortal infections. Between 2010 and 2015 more than 41 hospitals worldwide, most in the U.S., reported bacterial infections linked to the scopes, affecting 300 to 350 patients (http://www.modernhaelthcare.com/article/20160415/NEWS/160419937). It would be expected that a reduction in the bioburden in various medical devices would produce a concomitant overall reduction in infection rates and mortality. In addition, if endoscopes are not properly cleaned and dried, biofilm can build up on the lumen wall. Biofilms start to form when a free-floating microorganism attaches itself to a surface and surrounds itself with a protective polysaccharide layer. The microorganism then multiplies, or begins to form aggregates with other microorganisms, increasing the extent of the polysaccharide layer. Multiple sites of attachment can in time join up, forming significant deposits of biofilm. Once bacteria or other microorganisms are incorporated in a biofilm, they become significantly more resistant to chemical and mechanical cleaning than they would be in their free-floating state. The organisms themselves are not inherently more resistant, rather, resistance is conferred by the polysaccharide film and the fact that microorganisms can be deeply embedded in the film and isolated from any chemical interaction. Any residual biofilm remaining after an attempt at cleaning quickly returns to an equilibrium state and further growth of microorganisms within the film continues. Endoscopes lumens are particularly prone to biofilm formation. They are exposed to significant amounts of bioburden, and subsequent cleaning of the long narrow lumens is quite difficult due to inaccessibility and the inability to monitor the cleaning process.

There is considerable pressure in medical facilities to reprocess endoscopes as quickly as possible. Because endoscopes are cleaned by hand, training and attitude of the technician are important in determining the cleanliness of the device. Residual biofilm on instruments can result in a patient acquiring an endoscope acquired infection. Typically, these infections occur as outbreaks and can have fatal consequences for patients.

It is an object of the present invention to overcome or ameliorate at least one of the disadvantages of the prior art, or to provide a useful alternative.

SUMMARY OF THE INVENTION

According to one aspect, the present invention provides a cleaning apparatus for a medical device having one or more internal channels, the cleaning apparatus including:

at least two cleaning pumps adapted to pump a viscoelastic liquid, each pump having individual flow control, wherein each cleaning pump is fluidly connectable to the one or more of the internal channels such that the viscoelastic liquid can be pumped through the one or more internal channels thereby to remove contaminants.

A system for cleaning a medical device having one or more internal channels, the system including:

a consumable unit housing a viscoelastic liquid; and
a cleaning apparatus fluidly connectable to the consumable unit, the cleaning apparatus having at least two cleaning pumps adapted to pump the viscoelastic liquid, each cleaning pump having individual flow control, wherein each cleaning pump is fluidly connectable to one or more of the internal channels such that the viscoelastic liquid can be pumped through each of the one or more of said internal channels at a controlled flow rate thereby removing contaminants from the internal channels.

In one embodiment, the one or more internal channels include an internal surface and flowing the viscoelastic liquid removes contaminants from the internal surface.

In one embodiment, the controlled flow rate induces shear rate and/or strain on the internal surfaces thereby to remove contaminants from the internal surface.

In one embodiment, the at least two cleaning pumps are peristaltic pumps.

In one embodiment, the at least two cleaning pumps are diaphragm pumps.

In one embodiment, the one or more internal channels have a maximum allowable pressure and the viscoelastic liquid is pumped through each internal channel at or below the maximum allowable pressure.

In one embodiment, the apparatus includes a plurality of cleaning pumps, each cleaning pump being fluidly connectable to one internal channel of the medical device. Preferably, the plurality of cleaning pumps includes primary cleaning pumps and secondary cleaning pumps. More preferably, the primary cleaning pumps are fluidly connectable to the relatively larger channels in the medical device and the secondary cleaning pumps are fluidly connectable to the relatively smaller channels in the medical device.

In one embodiment, the apparatus includes a primary feed line for the primary cleaning pumps and a secondary feed line for the secondary cleaning pumps.

In one embodiment, the primary and secondary feed lines are selectively connectable to the viscoelastic liquid.

In one embodiment, the primary and secondary feed lines are selectively connectable to a supply of water.

In one embodiment, the primary and secondary feed lines include one or more proportional valves for controlling the flow of water.

In one embodiment, the cleaning apparatus is fluidly connectable to a consumable unit, the consumable unit housing the viscoelastic liquid.

In one embodiment, the consumable unit includes a booster pump for pumping the viscoelastic liquid to the apparatus.

In one embodiment, the apparatus includes a primary transfer conduit assembly and a secondary transfer conduit assembly for connecting the cleaning pumps to the internal channels.

In one embodiment, each the transfer conduit assembly includes one or more conduits, each conduit corresponding to one cleaning pump.

In one embodiment, each transfer conduit assembly includes a coupling connector, the connector being removably engageable with the cleaning pumps.

In one embodiment, the cleaning apparatus includes a coupling interface, and wherein each the coupling connector is removably engageable with the coupling interface.

In one embodiment, the medical device includes a plurality of internal channels.

In one embodiment, the pressure profile of the viscoelastic liquid flowing through the transfer conduit assemblies while pumping the viscoelastic liquid will be used to determine when the viscoelastic liquid has reached the entrance of the medical device.

In one embodiment, the change in the weight of the viscoelastic liquid housed in the reservoir is measured to verify if the correct amount has been used or not.

In one embodiment, the booster pump stops operating if the apparatus is disconnected from the consumable unit.

In one embodiment, the viscoelastic liquid has an expiry date, the expiry date being checked prior to the pumping through the one or more internal channels.

In one embodiment, the cleaning apparatus includes a barcode reader.

In one embodiment, the medical device is an endoscope.

In one embodiment, the system includes a primary transfer conduit assembly and a secondary transfer conduit assembly for connecting the cleaning apparatus to the one or more internal channels.

According to one aspect, the present invention provides a method of cleaning one or more contaminated internal channels of a medical device using a cleaning apparatus having two or more cleaning pumps and a supply of viscoelastic liquid, each cleaning pump being fluidly connectable to one or more of the contaminated internal channels, the method including the steps of:
 (i) flushing the one or more contaminated internal channels with a flushing liquid;
 (ii) pumping a viscoelastic liquid through the two or more internal channels at a controlled flow rate to remove contaminants; and
 (iii) rinsing the internal channel with flushing liquid.

In one embodiment, the flushing step (i) is omitted.

In one embodiment, the method further includes the step of purging the one or more internal channels with air.

In one embodiment, the controlled flow rate is adjusted by the speed of the at least one cleaning pump.

In one embodiment, the one or more internal channels include internal surfaces and pumping the viscoelastic liquid removes contaminants from the internal surfaces.

In one embodiment, the presence of the viscoelastic liquid, flushing liquid or air is confirmed using one or more optical sensors.

In one embodiment, the method includes the step of scanning a barcode associated with the medical device prior to step (i), and wherein upon scanning said barcode, operational cleaning parameters corresponding to the medical device are selected from sets of parameters stored in the apparatus.

In one embodiment, the method includes the step of measuring the flow rate of the rinsing liquid or the viscoelastic liquid using the one or more optical sensors associated with a logic control computer.

In one embodiment, the method includes the step of measuring the pressure of the rinsing liquid or the viscoelastic liquid using one or more pressure sensors associated with the logic control computer.

In one embodiment, prior to step (i), the rinsing liquid is heated to a preselected temperature.

In one embodiment, the flushing liquid is water.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

DESCRIPTION OF FIGURES

Preferred embodiments of the invention will now be described, by way of example only, with reference to the accompanying drawings in which.

DESCRIPTION OF PREFERRED EMBODIMENTS

Figure 1:
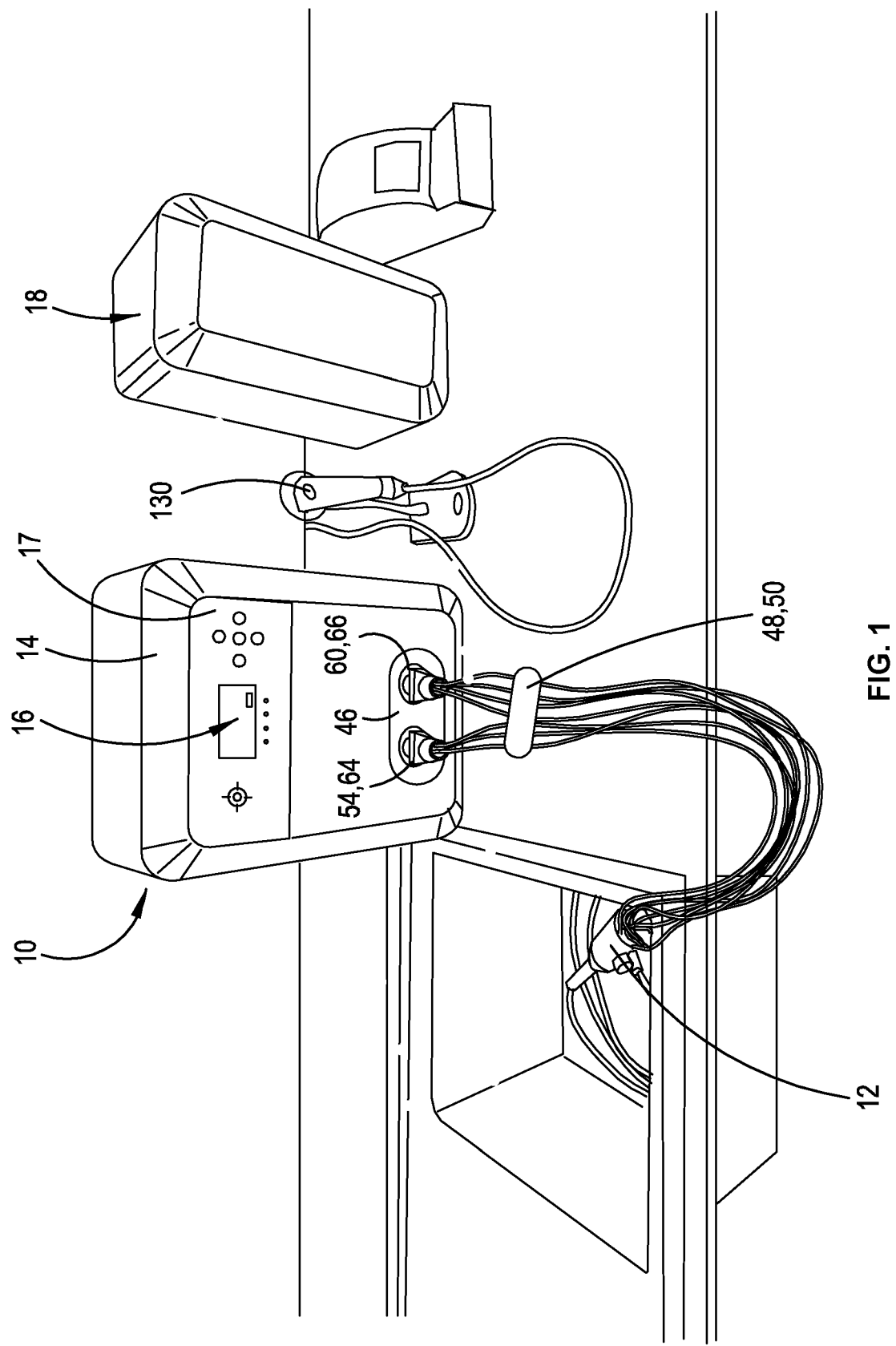
FIG. 1 is a perspective view of the cleaning apparatus of the present invention connected to a medical device.

Exemplary embodiments of the present invention will now be described in detail with reference to the accompanying drawings. In the drawings, the same elements are denoted by the same reference numerals throughout. In the following description, detailed descriptions of known functions and configurations incorporated herein have been omitted for conciseness and clarity.

With reference to the accompanying drawings and initially to FIG. 1, there is provided a cleaning apparatus 10 for a medical device 12 according to the present invention, the medical device having one or more internal channels. The cleaning apparatus includes a main housing 14 with display 16 and user control buttons 17. As shown, connected to one side of the cleaning apparatus 10 is a consumable unit 18, which houses a cleaning agent, and on the other side, to the medical device 12 to be cleaned.

Figure 2:
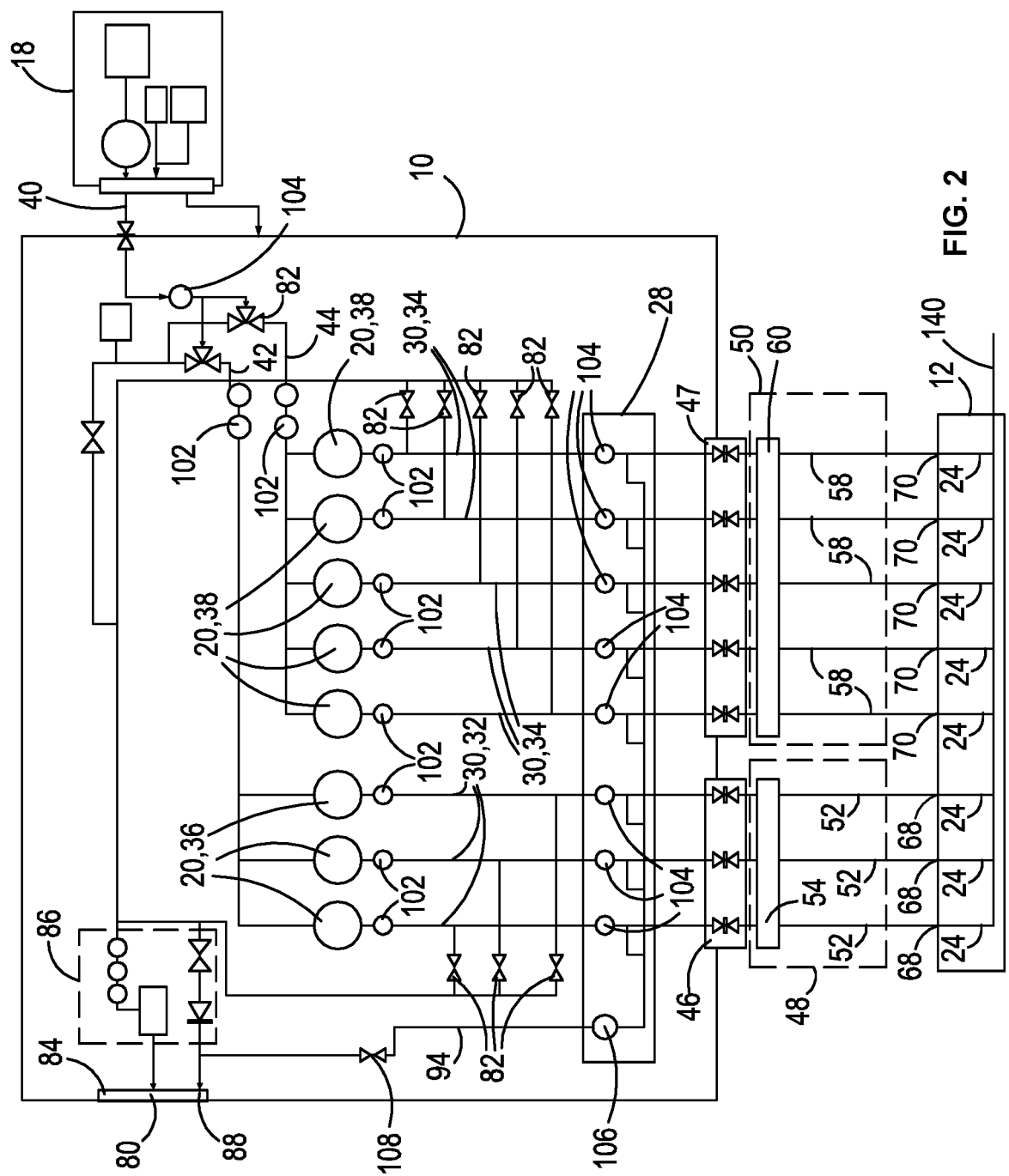
FIG. 2 is a schematic view of the cleaning apparatus of FIG. 1.

The cleaning apparatus includes at least two cleaning pumps 20 as shown in FIG. 2. In the illustrated embodiment, each cleaning pump 20 is an individually controllable variable speed peristaltic type pump having the ability to pump a cleaning agent in the form of a viscoelastic liquid 22. In a further embodiment, each cleaning pump is an individually controllable diaphragm pump, or other individually controllable pump suitable to pump a viscoelastic liquid 22. Each cleaning pump 20 is fluidly connectable to one or more internal channels 24 in the medical device 12.

In the embodiment illustrated in FIG. 2, each cleaning pump 20 is fluidly connectable to a corresponding internal channel 24 in the medical device 12. By way of this connection, the viscoelastic liquid can be pumped into each channel thereby removing contaminants. More specifically, the internal channels 24 include internal surfaces 26 and the viscoelastic liquid 22 is individually pumped through each internal channel 24 under conditions of controlled volumetric flow and pressure to induce a shear rate and/or strain to remove contaminants from the surfaces 26.

Using this method, the viscoelastic liquid is flowed through each of the channels and moves in a predominantly elastic state providing mechanical forces to internal surfaces of the endoscope thereby pushing soils or other contaminants out.

In one embodiment, a viscoelastic liquid 22 comprises dissolved and/or dispersed chemicals in a carrier fluid, the carrier fluid being selected to provide a suitably stable formulation. Suitable carrier fluids include water, alcohols, glycols or their mixtures, or any other suitable fluids. This viscoelastic liquid 22 may also be a viscoelastic polymeric water-based system or any other viscoelastic system. It may also contain additional functional additives, like rheology modifiers, high surface area inorganic materials, dispersing agents, surfactants, emulsifiers, solvents or other functional ingredients to enhance the cleaning efficacy. These can include abrasive particles or particles with adsorbent properties.

The viscoelastic liquid 22 may contain other functional ingredients like rheology modifiers, high surface area adsorbing materials, surfactants, dispersing agents, emulsifiers, solvents or suspended inorganic/organic particles. This viscoelastic liquid behaves largely as fluid with elasticity modulus (G') dominating. The viscoelastic liquid may contain other additives to assist in cleaning. However, it is important to note that the viscoelastic liquid of the present invention excludes microfibrils or other additives that may affect the rheology and result in the viscoelastic liquid having a liquid flow rather than a cohesive plug flow.

In one embodiment, the viscoelastic liquid is flowable and water based with optimised rheology containing dispersed polymers and high surface area hydrophilic fumed silica. Nanoparticles of silica in the range of 10-100 nm, or more preferably 20-70 nm have been shown to be useful in the removal of biofilm.

Figure 3:
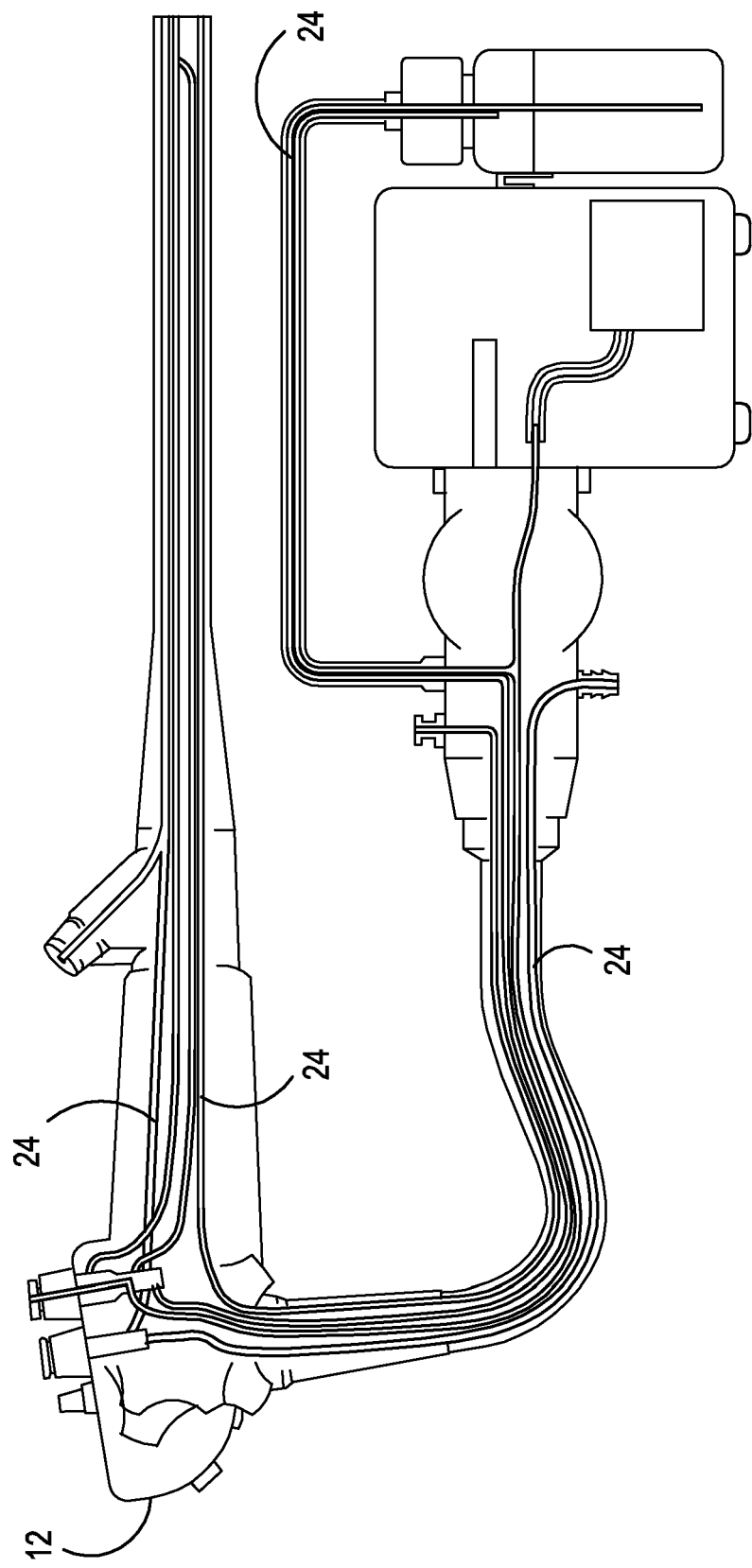
FIG. 3 is a cross-sectional view of the medical device of FIG. 1.

Referring to now FIG. 3, the medical device according to the illustrated embodiment is an endoscope 12 having a plurality of internal channels 24 in the form of one or more elongate lumens, suction valve cylinders, air/water cylinder or biopsy ports. Those familiar with the art will appreciate that the term 'endoscope' may include gastroscopes, bronchoscopes, colonoscopes, pleuroscopes, EBUS (Endobronchial Ultrasound), intubation scopes, laryngoscopes, rhino laryngoscopes, cystoscopes, ureteroscopes, and hysteroscopes. Given these various types of endoscopes, the contaminants to be removed may include one or more of flesh, blood, mucous, faeces, biofilms or lubricants.

It should be appreciated that flowing a viscoelastic liquid may cause damage to the internal channels of the endoscope if the pressure and/or velocity provided by flowing the viscoelastic liquid is too high. This is especially the case where some of the internal channels have a relatively small diameter and are therefore substantially susceptible to damage due to excessive pressure. Similarly, flowing a viscoelastic liquid through the internal channels at a too high a velocity may result in some of the internal surfaces being missed or contacted with insufficient shear force to effectively remove contaminants. In a similar vein, flowing a viscoelastic liquid at an insufficient pressure and/or velocity, may also result in an excessive time to clean the channels.

Accordingly, returning now to FIG. 2, the cleaning apparatus 10 of the illustrated embodiment, includes eight peristaltic cleaning pumps 20, each being fluidly connectable to one internal channel 24 of the endoscope 12 to provide precise flow of the viscoelastic liquid. This individual connection allows for individual and controllable fluid flow of a pumped liquid through each channel, which results in controllable individual shear rate and strain of each internal surface 26. If an endoscope has less than eight internal channels, then only a corresponding number of cleaning pumps 20 will be connected and activated to clean that endoscope.

Those familiar with the art will appreciate that a peristaltic pump is a positive displacement pump ideally suited to viscoelastic and other viscous liquids. A peristaltic pump also has ability to efficiently pump water at various temperatures. They are also commonly referred to as roller pumps, whereby the liquid to be pumped is contained within a flexible tube fitted inside a circular pump casing. A rotor having a number of circumferentially disposed rollers compress and pinch the flexible tube as the rotor turns. This action results in the liquid being forced through the tube. This process is called peristalsis and is used in many biological systems such as the gastrointestinal tract. Peristaltic pumps are ideally suited to the application of the present invention as they provide a large range of flow rate and more specifically, are able to maintain their pressure at very slow pumping rates. It should be also appreciated that the viscoelastic liquid rheology may be permanently destroyed if exposed to high shear forces. For this reason, peristaltic pumps advantageously apply a low shear rate on the viscoelastic liquid during pumping and liquid displacement.

Each peristaltic cleaning pump 20 is fluidly connected to an exit manifold 28 by way of eight supply lines 30. In the present embodiment, the supply lines 30 are split into a group of primary supply lines 32 and a group of secondary supply lines 34. As discussed in further detail below, the primary supply lines 32 lead from a group of primary cleaning pumps 36 and the secondary supply lines 34 lead from a group of secondary cleaning pumps 38. The primary supply lines 32 and primary cleaning pumps 36 are adapted to be connected to the relatively larger internal channels in the endoscope 12, and the secondary supply lines 34 and secondary cleaning pumps 38 are adapted to be connected to the relatively smaller internal channels of the endoscope 12.

In the illustrated embodiment, the primary cleaning pumps are provided viscoelastic liquid 22 from the consumable unit 18, exterior of the apparatus 10, through a main feed line 40. This main feed line 40 is then split into a primary feed line 42 for supplying viscoelastic liquid to the primary cleaning pumps 36, and a secondary feed line 44 for supplying viscoelastic liquid to the secondary cleaning pumps 38.

To allow for the connection to the endoscope 12, the exit manifold 28 is fluidly connected to a primary coupling interface 46 and a secondary coupling interface 47 located on the edge of the cleaning apparatus 10. From the primary coupling interface 46 and secondary coupling interface 47, connection to the endoscope 12 is facilitated by a primary transfer conduit assembly 48 and a secondary transfer conduit assembly 50.

The primary transfer conduit assembly 48 includes a group of primary conduits 52, a colour-coded primary coupling connector 54 for connecting the primary conduits to the primary coupling interface 46, and primary endoscope connectors 56 for connecting to the internal channels of the endoscope 12. Similarly, the secondary transfer conduit assembly 50 includes a group of secondary conduits 58, a colour-coded secondary coupling connector 60 for connecting the secondary conduits to the secondary coupling interface 47, and secondary endoscope connectors 62 for connecting the secondary transfer conduits to the internal channels 24 of the endoscope 12. The cleaning apparatus 10 may be provided with several combined primary and secondary transfer conduit assemblies. Each transfer conduit assembly corresponding to, and being connected to the apparatus 10, at the time of connection of each endoscope type.

The primary transfer conduit assembly 48 is used for connection between the primary cleaning pumps 36 and the relatively larger internal channels of the endoscope, and the secondary transfer conduit assembly 50 is used for connection between the secondary cleaning pumps 38 and the relatively smaller internal channels of the endoscope 12.

Each endoscope connector is adapted to be releasably engageable with a corresponding inlet receiving apertures on the endoscope 12. In one embodiment, the inlet receiving apertures on the endoscope are defined by primary inlet apertures 68 and secondary inlet apertures 70.

It should be appreciated that the cleaning pumps, supply lines, and fluid conduits are grouped into primary and secondary groups to allow for the internal channels 24 having different flow rate and pressure limit requirements due to having different cross-sectional areas. More particularly, as the primary transfer conduit assembly 48 is connected to the larger channels in the endoscope 12 during cleaning, the volumetric flow rate for the primary cleaning pumps 36 will be relatively higher than the secondary cleaning pumps 38 to maintain the same flow velocity through each of the channels. Similarly, the smaller internal channels have a lower volumetric flow rate.

The cleaning apparatus 10 is also connectable to mains water supply 80. The water supply 80 is fluidly connected to a plumbing interface 84, which delivers the mains water to either the primary feed line 42 and secondary feed line 44 upstream of the cleaning pumps, or directly to the primary supply lines 32 and secondary supply lines 34 downstream of the cleaning pumps. In this way, mains water may be provided directly to each internal channel, or alternatively/additionally, delivered to the inlets of each of the cleaning pumps 20 to then be pumped into each of the internal channels at a desired volumetric flow rate.

As part of the water supply system within the cleaning apparatus 10, a water loop 86 has also been provided. As discussed in more detail below, water loop 86 is used to circulate the mains water supply in and out of the cleaning apparatus via a drain 88 until the desired water temperature is reached. This warmed water may be then delivered to the upstream ends of the cleaning pumps or may bypass the cleaning pumps to directly feed to the primary supply lines 32 and secondary supply lines 34. Alternatively, when a preselected water temperature is not required, the water may be delivered at mains temperature.

In the event that the installation location does not have mains water with a hot water mixing function, in a further embodiment (not shown), a mixing valve feeding from a hot and cold-water connection, external the cleaning apparatus, and a computer-controlled water booster pump are provided to supply water at a controlled temperature.

As mentioned earlier, plumbing interface 84 also provides a connection to a drain 88, which is typically in the form of an outlet in the plumbing interface leading to a drain connection under a normal sink. From the plumbing interface, drain 88 is fluidly connected to drainage line 94, which leads from exit manifold 28 through valve 108. As discussed in more detail below, the drainage line 94 is used as part of the cleaning process if there is an excess pressure detected. The drain 88 also provides an alternative path from the cleaning pumps 20 to the outside of the device. This is very helpful for flushing and cleaning the internal components of the cleaning apparatus during maintenance cycles.

A plurality of optical sensors 102 positioned in the upstream end of the primary supply lines 32 and the upstream ends of the secondary supply lines 34 is also provided. Optical sensors 102 are also provided on the primary feed line 42 and the secondary feed line 44.

The cleaning apparatus 10 further includes a main logic control computer 100 (not shown) to control all the cleaning pumps 20, shut off valves, to read all the optical and pressure sensor data, and to operate the programmed cleaning sequence based on the operational parameters of the selected endoscope. The main logic control computer 100 also operates a main display screen 16 and therefore provides the user instructions and receives input from user control buttons 17. The consumable unit 18 also includes a supplementary control computer 200 (not shown), which communicates with the main logic control computer 100 on the cleaning apparatus.

According to the invention, the optical sensors 102 cooperate with the main logic computer 100 to perform several functions during the operation of the cleaning apparatus 10. In one application, the optical sensors determine the presence of either the viscoelastic liquid, or other cleaning agent, water, or air in the respective supply or feed line. This information is then fed back to the main logic control computer 100. In a further application, using the optical sensors in the feed lines and in the supply lines, the flow rate of liquid being pumped through each of the cleaning pumps can be determined based on a differential time calculation upstream and downstream of the cleaning pumps.

In one embodiment, the optical sensors are calibrated by the logic control computer 100 by flow water through the primary and secondary supply lines and adjusting the electrical current of the optical sensors to correspond to the value for water.

Similarly, the cleaning apparatus 10 of the present invention includes a plurality of pressure sensors 104 located primarily in the downstream portions of the primary supply lines 32 and secondary supply lines 34. A further pressure sensor 104 is provided in the main feed line 40 to determine the pressure of the viscoelastic liquid being delivered from the consumable unit 18. Pressure sensors 104 are also provided in the water supply lines and drain supply lines. The main function of the pressure sensors 104 is to measure pressure at specific points and send this information back to the main logic computer 100. In this way, each stage of the cleaning process can be identified.

The pressure sensors 104 also cooperate to detect if the endoscope is connected to the cleaning apparatus and senses if there are any blockages in the system. In those circumstances, a fault condition will be generated by the main logic control computer, and an indication is sent back to the user via display 16.

Figure 4B:
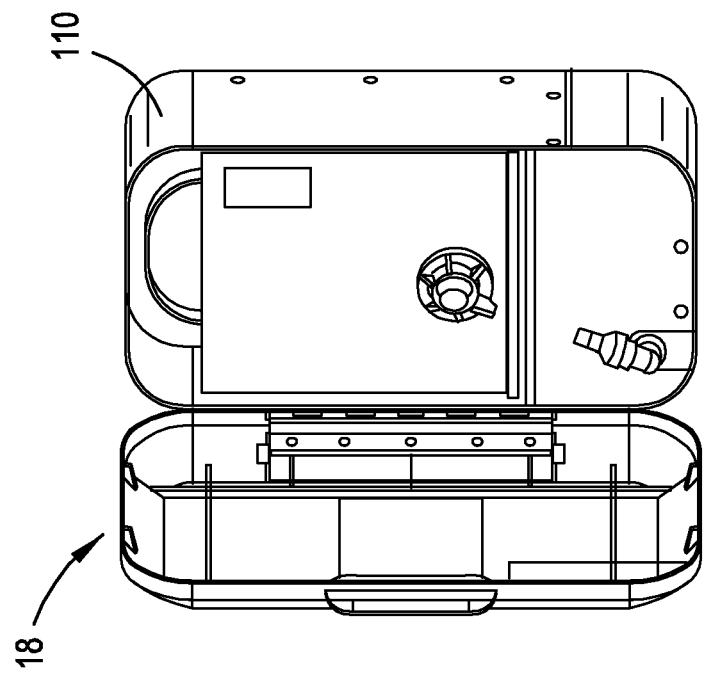
FIG. 4b is a perspective view of a consumable unit for use with the cleaning apparatus of FIG. 1.
Figure 4A:
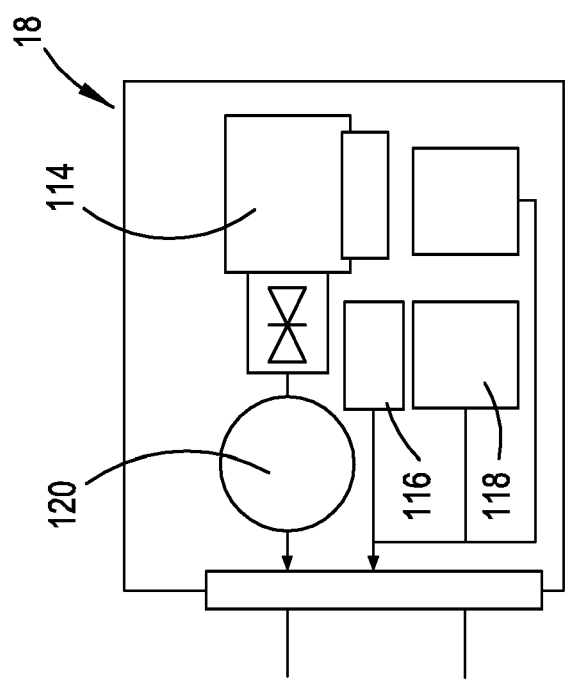
FIG. 4a is a schematic view of a consumable unit for use with the cleaning apparatus of FIG. 1.

Referring now to FIGS. 1, 4a and 4b, in the illustrated embodiment, the cleaning apparatus 10 is fluidly connectable to the consumable unit 18, which houses the viscoelastic liquid 22. Whilst not wishing to limit the use of the invention to one application, it is proposed that cleaning apparatus 10 be installed in surgeries, hospitals, or other medical practice areas, close to where endoscopes would be used. Those familiar with these procedures will appreciate that bench space in such areas is usually limited. It is for this reason, that the consumable unit 18 is separately provided to cleaning apparatus 10. Advantageously, this allows the cleaning apparatus 10 to be of a smaller footprint than would be required if it incorporated the consumable unit 18 thereby freeing up bench area. The consumable unit 18 can be placed in any position that is convenient and, in some cases, can be located under a sink.

As best shown in FIG. 4a and FIG. 4b, the consumable unit 18 includes a housing 110 having a door 112. Inside the housing 110 is a consumable reservoir 114 for the viscoelastic liquid 22. A load cell 116 is provided to measure the weight of the consumable reservoir 114 thereby allowing confirmation of the amount of viscoelastic being used during the cleaning process. An interlocked door sensor 118 is also provided to make sure that the door is closed before the cleaning process can begin.

Those familiar with this art will note that the peristaltic cleaning pumps 20 of cleaning apparatus 10, or a diaphragm pumps according to an alternative embodiment, are typically not designed to have a high suction pressure capacity, rather, they are designed to have a higher discharge capacity amongst other features. For this reason and according to the illustrated embodiment, a booster pump 120 has been provided in the consumable unit 18. The booster pump, which is also controlled by main logic control computer 100 and may also be a peristaltic or diaphragm type pump, draws viscoelastic liquid from the consumable reservoir 114 and delivers it to the cleaning pumps 20 through main feed line 40. In this way, the peristaltic cleaning pumps 20 are not required to have high suction capacity and therefore can be smaller in size. By having smaller pumps, the overall size of the cleaning apparatus 10 can be advantageously reduced. Also, the provision of a booster pump 120 allows the consumable unit 18 to be placed in any position that is convenient to the user's application, while the cleaning apparatus 10 can be placed close to a sink so that viscoelastic liquid used in the cleaning process can flow out of the endoscope directly into the sink. In a further not shown embodiment, the consumable unit includes a second cleaning agent or flushing liquid such as a detergent, housed in a second reservoir 214.

Returning to FIG. 1, the cleaning apparatus 10 further includes a barcode reader 130 for reading a barcode corresponding to the endoscope to be cleaned and establish the operational parameters for the cleaning apparatus. The barcode may be located on the endoscope itself or its packaging or may be in a physical or online operational manual corresponding to the model number and brand of the endoscope 12.

In operation, the user scans the barcode corresponding to the endoscope 12 and the cleaning apparatus automatically recalls the operational parameters from the logic control computer's memory and establishes the operational cleaning program for the model of endoscope corresponding to the barcode. Amongst other features, these operational parameters are based on the number of endoscope connections to be used on the endoscope, and which primary transfer conduit assembly 48 and secondary transfer conduit assembly 50 to use. The operational parameters may also allow for the size of each of the internal channels, the maximum pressure allowable in each internal channel, flush and rinse temperature, viscoelastic liquid volumetric flow rate, number of endoscope channels, pressure limits for blockage and leakage detection, and the operational cleaning process for the endoscope as discussed further below.

In use, the cleaning apparatus 10 is first switched on by user activation of buttons 17. The user display 16 then instructs the user to scan the barcode of the endoscope to be cleaned so that the correct operational cleaning parameters are recalled from the main logic control computer's memory. The user then selects a predefined primary transfer conduit assembly 48 and secondary conduit transfer assembly 50 as instructed by the user display 16.

The user then engages the primary coupling connector 54 with the primary coupling receiver 46 and the secondary coupling connector 60 is engaged with the secondary coupling receiver 47, on the cleaning apparatus. Since the primary and secondary coupling connectors and the primary and secondary coupling receivers are colour coded, this connection will be a relatively simple action for the user.

The primary endoscope connectors 56 are then engaged with each of the primary inlet apertures 68 on the endoscope 12, and the secondary endoscope connectors 62 with each of the secondary inlet apertures 70. Once these connections are made, the automatic cleaning process can begin by user activation based on instructions on the user display 16. It should be appreciated that separate user activation is required in accordance with most regulatory requirements.

Figure 5:
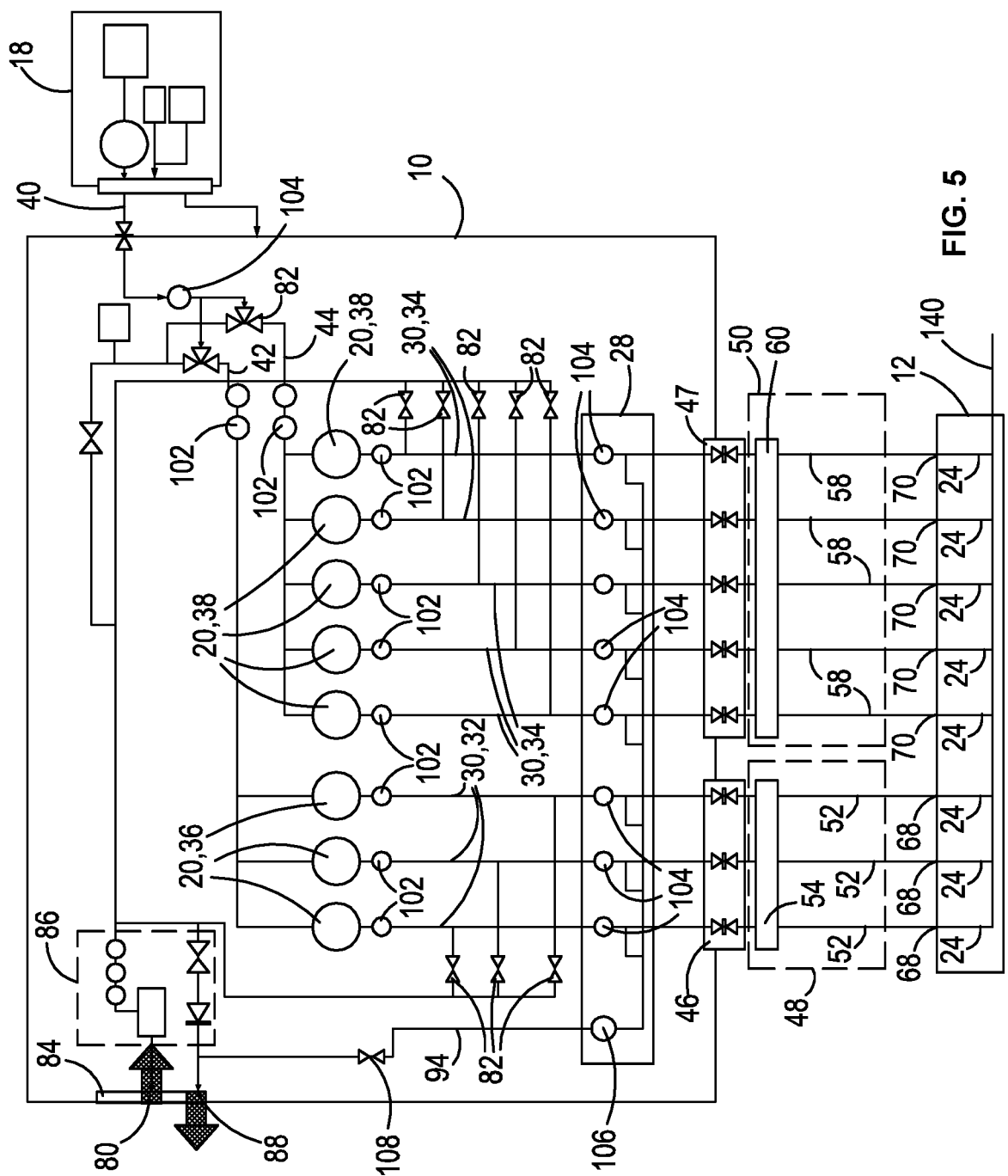
FIG. 5 is a schematic view of the cleaning apparatus of FIG. 1, depicting mains water flowing through a water loop to a preselected temperature.

With reference to FIG. 5, the first step in the automatic cleaning process is the warm water flush. In this step, mains water supply 80 enters through plumbing interface 84 and is looped through water loop 86 until the preselected temperature is reached.

Figure 6:
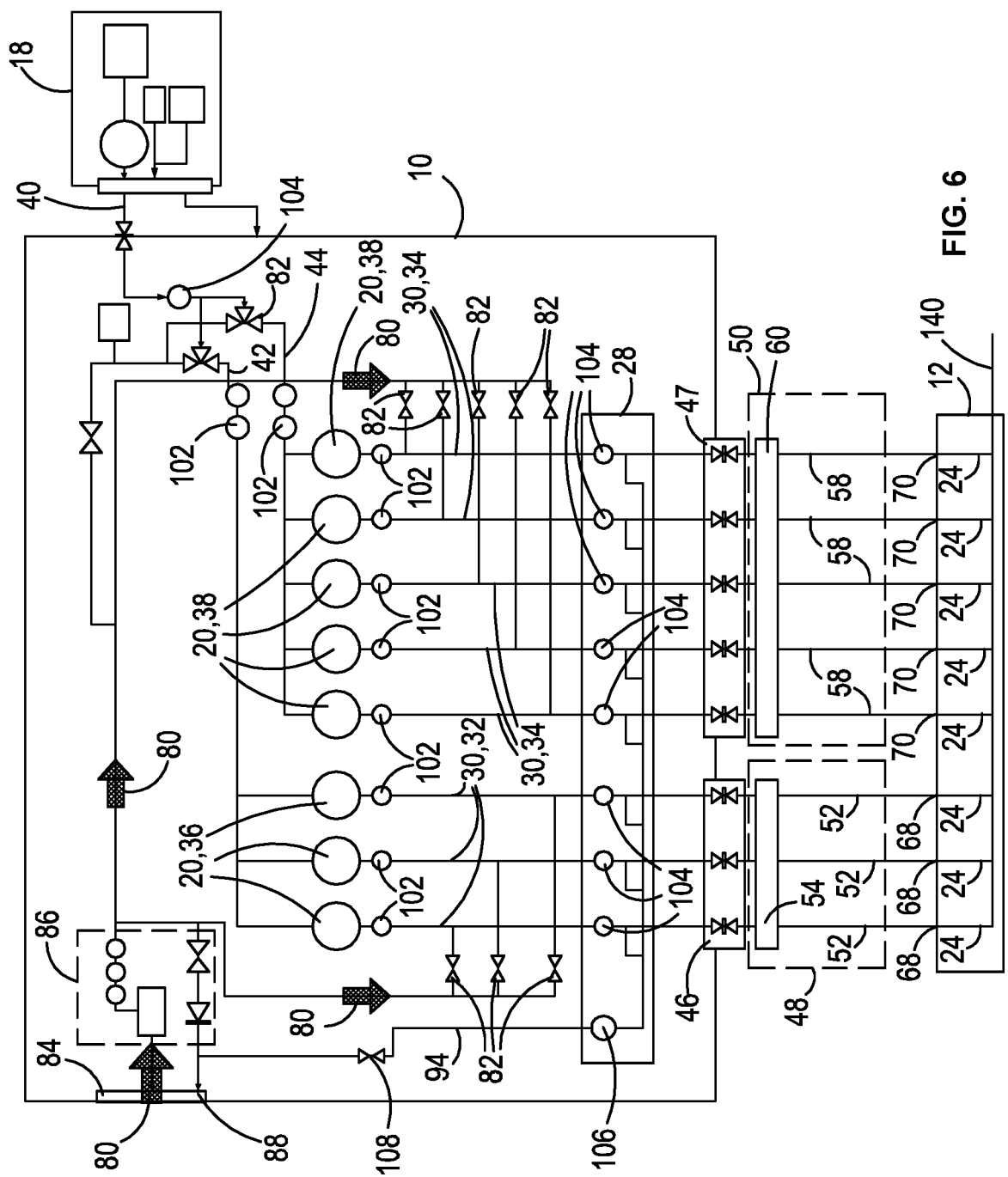
FIG. 6 is a schematic view of the cleaning apparatus of FIG. 1, depicting warm water flowing directly to the medical device.

With reference now to FIG. 6, once the preselected temperature is reached, shut off valves 82 are opened, and the warmed mains water 80 is directed to primary supply lines 32 and secondary supply lines 34 as shown. Warm water then enters each of the internal channels 24 of the endoscope 12 via the primary conduits and secondary conduits, typically at a maximum velocity and below the maximum pressure limit of the respective internal channel.

As the warm water passes through each of the internal channels, the relatively larger sized contaminants will be removed and passed out of the endoscope 12 through a common port 140. Importantly, it should be appreciated that the velocity of the water flow at this step corresponds to the maximum flow rate allowable in each internal channel. Further, the temperature of the warm water has been set such that it will wet and soften the contaminants not removed but will not be so hot as to coagulate and harden the remaining contaminants.

Figure 7:
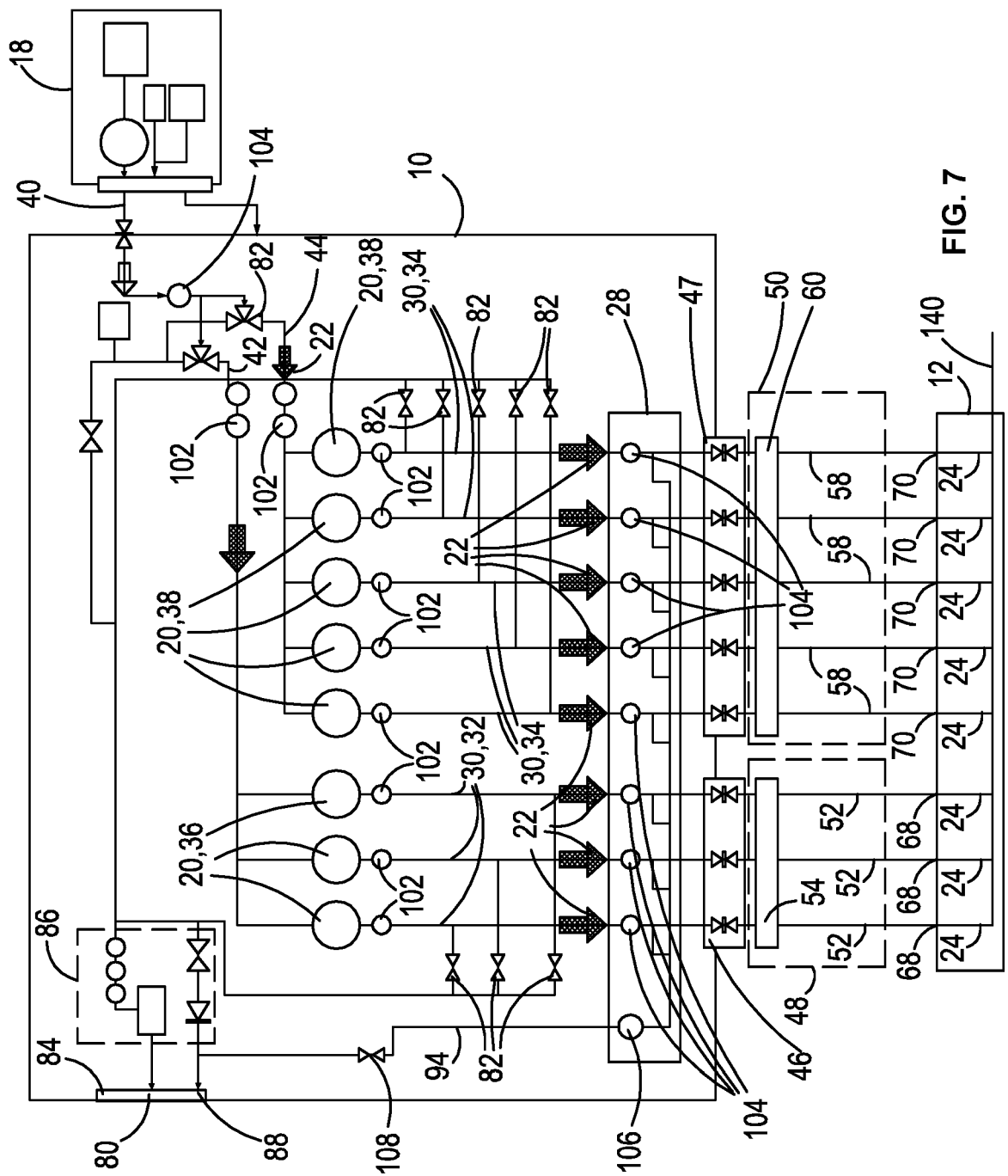
FIG. 7 is a schematic view of the cleaning apparatus of FIG. 1, depicting viscoelastic liquid being delivered to, and being pumped by, the cleaning pumps.

With reference now to FIG. 7, once the internal channels have been flushed with warm water, the next step in the automatic cleaning process is the priming of the primary and secondary supply lines and conduits with viscoelastic liquid 22 cleaning agent. In an alternate embodiment or variation to operational parameters of the cleaning apparatus, the flushing step is omitted, and the first step in the cleaning process is the priming of the primary and secondary supply lines and conduits with viscoelastic liquid 22 cleaning agent. To do this, the viscoelastic liquid weight is first measured in the consumable unit 18. As mentioned earlier, the weight of the viscoelastic liquid is monitored to verify if the correct amount of viscoelastic liquid is being used at each stage of the cleaning process. Further, at this point, the consumable unit 12 will check the expiry date of the viscoelastic liquid to make sure it is within operational use parameters. If it the operational date is beyond the expiry date, a fault condition will be triggered and displayed on user display 16.

Assuming the viscoelastic liquid is in operational condition, booster pump 120 then activates and pumps the viscoelastic liquid through the main feed line 40. If the communication between the cleaning apparatus 10 and consumable unit 12 is broken, the booster pump 120 will cease to activate.

The viscoelastic liquid 22 is then separated into the primary feed line 42 and secondary feed line 44 and delivered to the upstream ends of the cleaning pumps 20. The pressure of the viscoelastic liquid 22 at the upstream ends of the primary and secondary cleaning pumps is measured using pressure sensors 104 and, if required, the main control logic computer 100 adjusts the speed of the booster pump 120 in order to achieve the target pressure at the pump inlets, which is ideally close to zero. It should be appreciated that without the booster pump the primary and secondary cleaning pumps would experience large losses and there would not be a predictable relationship between each pump's rotational speed (rpm) and the volumetric flow rate generated.

In most cases, prior to preliminary start-up of device 10, feed lines 40, 42, & 44 connecting the cleaning device 10 and consumable unit 18 are filled with the viscoelastic liquid 22 from a previous operation, so that there are no delays after the warm water flush. If it is found that the viscoelastic liquid inside the consumable unit or the apparatus lines has expired, they will be purged to the drain 94 through the feed line 40, 42, 44, cleaning pumps 20, and exit manifold 28 as soon as a fresh viscoelastic liquid is loaded into the consumable unit 18. Alternatively, the main feed line is filled with viscoelastic liquid during the initial flushing stage.

Since the main feed line is already filled with the viscoelastic liquid 22, at the same time as the pumping of viscoelastic liquid from the booster pump 120, the primary cleaning pumps 36 and the secondary cleaning pumps 38 activate and respectively pump an individual and predetermined volume of viscoelastic liquid through each of the supply lines 30. The amount of viscoelastic liquid pumped by any of the active cleaning pumps will depend on the operational parameters in the cleaning apparatus. As a result, the viscoelastic liquid is pumped through the primary and secondary supply lines through the primary and secondary conduits and towards the inlet apertures of the endoscope. It should be appreciated that main control logic computer 100 continually monitors the flow rate of the pumps using the optical sensors 102.

This step is often referred to as coupling priming because it delivers the viscoelastic liquid 22 to the start of each of the internal channels 24, whereby the viscoelastic liquid is primed and ready to be delivered to the internal channels 24 at the preselected flow rate. The flow rate of the viscoelastic liquid 22 is centrally adjusted by the speed of the respective peristaltic pumps 20. Until the viscoelastic liquid 22 enters the inlet apertures 24, it is pumped at a relatively high flow rate to minimise cleaning cycle times. When the liquid 22 enters the internal channels, the respective cleaning pumps adjust the volumetric flow rate to achieve the ideal contaminant removal.

Figure 8:
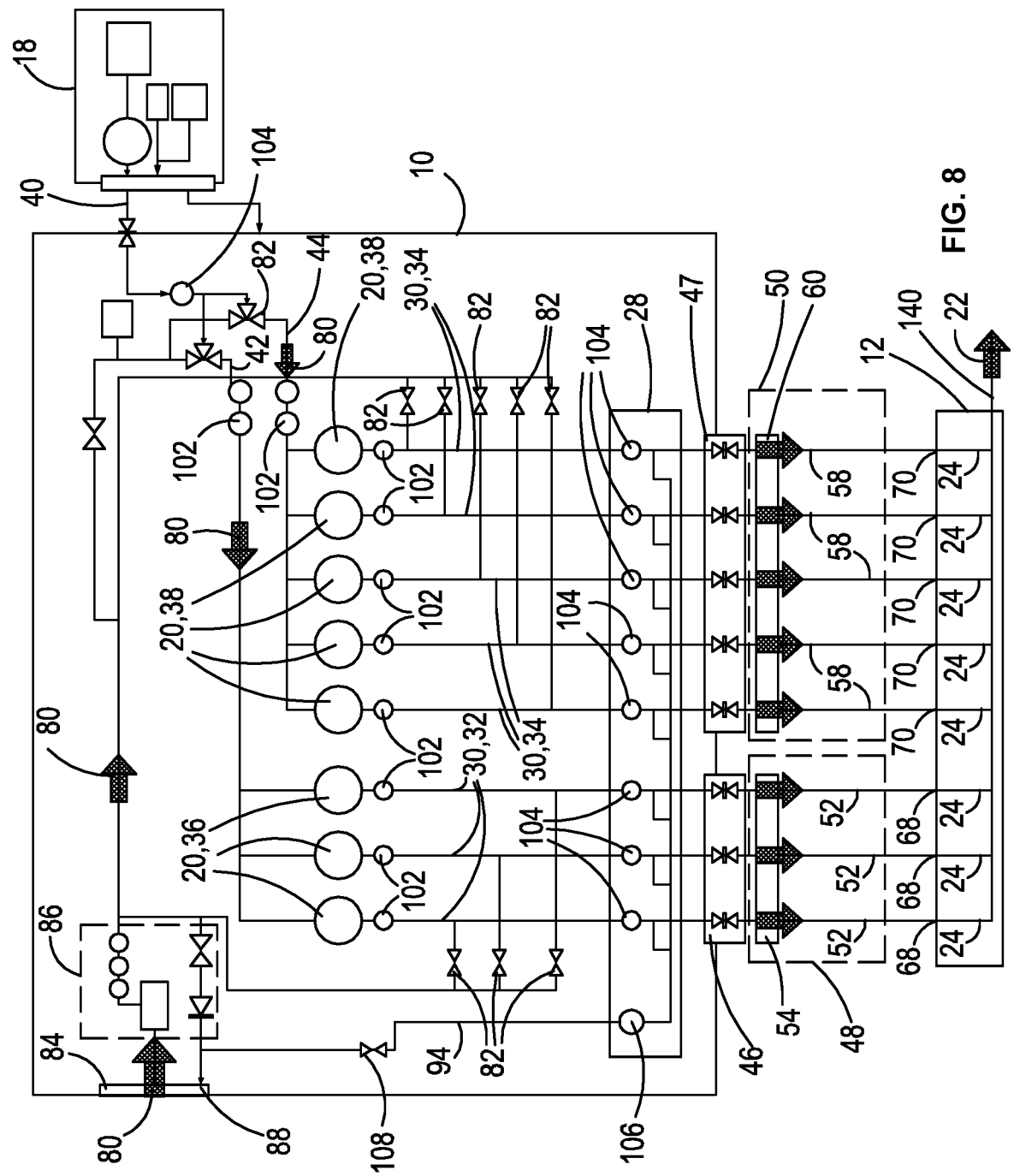
FIG. 8 is a schematic view of the cleaning apparatus of FIG. 1, depicting water being delivered to the cleaning pumps.

With reference now to FIG. 8, once a predetermined amount of viscoelastic liquid has been pumped through each of the cleaning pumps, the relevant shut-off valves are activated, and viscoelastic liquid supply to the upstream end of the primary and secondary cleaning pumps is replaced with mains water 80 to continue the priming. That is, mains water 80 is now pumped by the primary and secondary cleaning pumps to push up against the viscoelastic liquid 22 so that it can continue flowing. The flow rate of the water through each of cleaning pumps is individually adjusted to the required flow rate of the viscoelastic liquid 22 though the respective internal channel.

In one variation of this embodiment, at this stage, mains water 80 is supplied to the upstream end of the primary cleaning pumps 36, whilst viscoelastic liquid 22 is still being provided to the upstream end of the secondary cleaning pumps 38. Alternatively, in a further variation, water is supplied to the upstream end of the secondary cleaning pumps 38 whilst viscoelastic liquid is still being provided to the upstream end of the primary peristaltic pumps 36. Both these variations may be required in order to optimise the cleaning time process based on each endoscope cleaning requirements.

In the illustrated embodiment, the pressure sensors 104 are used to determine the pressure of the viscoelastic liquid flowing through the transfer conduits during pumping. In this way, the pressure profile can be determined and the main logic control computer 100 will know when the viscoelastic liquid has reached the inlet apertures of the endoscope 12.

Once the viscoelastic liquid 22 reaches the inlet apertures of the endoscope 12, either by being pushed by pumped water or by continued viscoelastic liquid pumping, its flow rate is individually altered so that the viscoelastic liquid can proceed through each of the internal channels 24 at a preselected volumetric flow rate. This preselected volumetric flow rate is individually controlled by each cleaning pump to correspond to the programmed ideal volumetric flow and pressure for the respective internal channel. More specifically, the flow rate has been predetermined so that the viscoelastic fluid travels through each of the internal channels 24 to create enough shear force against the internal surfaces 26 of the internal channels to remove the contaminants. At the same time, the flow of the viscoelastic liquid must not exceed the maximum internal pressure limit of the internal channel. In this regard, the flow rate of the viscoelastic liquid travelling through each internal channel is optimised according to its diameter to achieve both these outcomes.

As the viscoelastic liquid is pumped through the internal channels at a volumetric flow rate that results in a shear rate below its yield point, the viscoelastic liquid moves in its predominantly elastic state providing mechanical forces to the internal surfaces of the endoscope and pushing contaminants out through common port 140. The viscoelastic liquid 22 by itself has no abrasion properties and therefore will not damage the internal channels or any of the seals in the endoscope. Once the viscoelastic liquid 22 has completed its path through the internal channels, it exits through the common port 140 in the endoscope 12.

Figure 9:
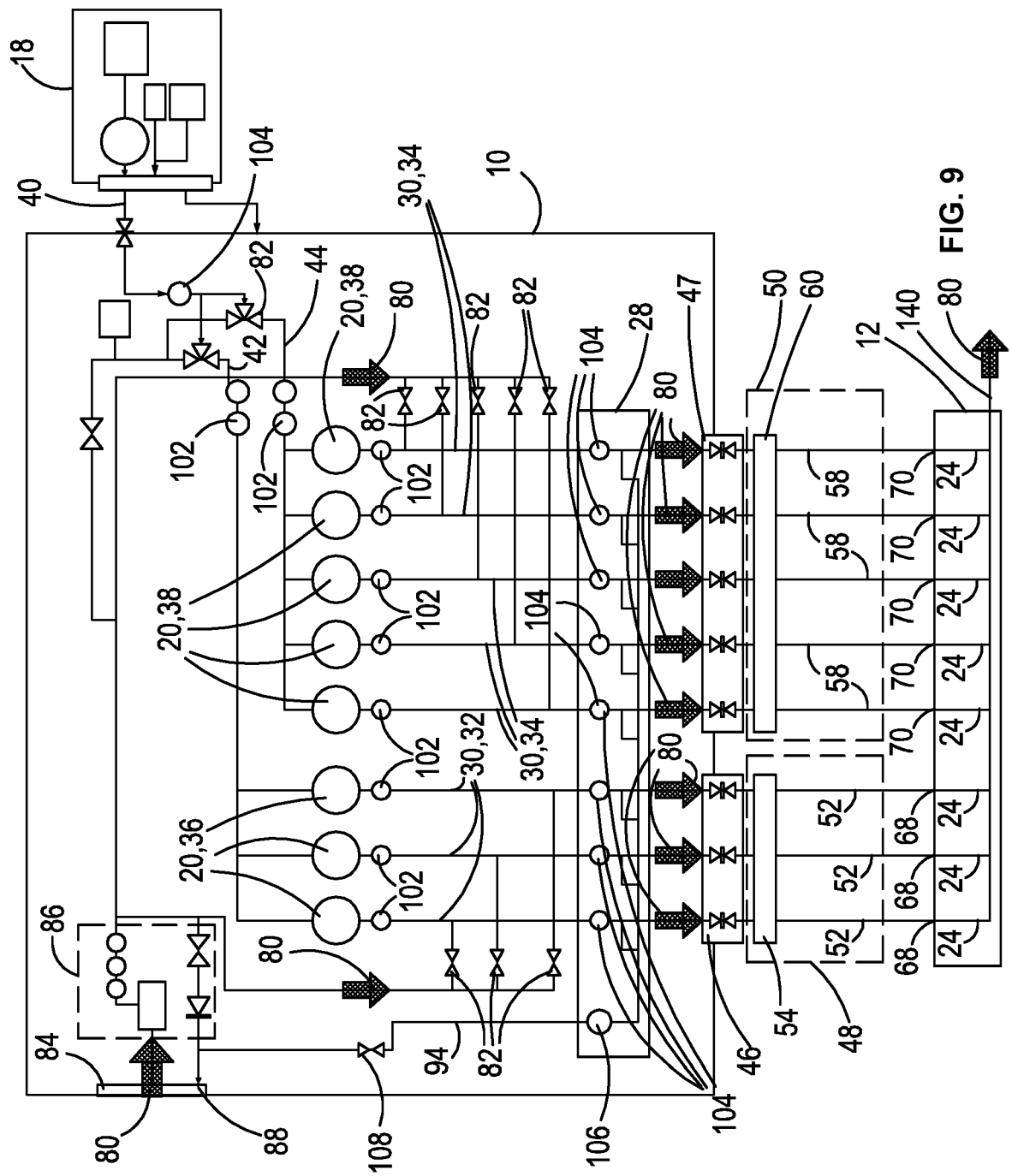
FIG. 9 is a schematic view of the cleaning apparatus of FIG. 1, depicting mains water being delivered directly to the medical device.

Referring now to FIG. 9, once the viscoelastic liquid has completely passed through each internal channel 24 of the endoscope 12, the flushing step can begin. In this step, shut-off valves 82 are again activated, and mains water 80 is delivered directly first through the primary supply lines 32 and then later through the secondary supply lines 34. Each of the internal channels is then flushed out through common port 140 to remove any remaining viscoelastic liquid.

In one embodiment, due to the smaller internal channels and the secondary supply lines 34 representing a larger fluidic resistance, the flow rate of viscoelastic liquid 22 through these internal channels 24 will be lower. For this reason, the flushing of the larger internal channels, connected to the primary cleaning pumps 36, will normally begin prior to the completion of viscoelastic liquid passing through the smaller internal channels. Under these circumstances, the primary cleaning pumps 36 will stop pumping and mains water is directly channeled to the primary supply lines 32, downstream of the primary cleaning pumps 36. At the same time, the secondary cleaning pumps 38 are still pumping water, or in some cases viscoelastic liquid, to push the viscoelastic liquid 22 through the smaller internal channels. Once the viscoelastic liquid has passed through the smaller internal channels, the secondary cleaning pumps 38 deactivate and mains water 80 is then directly connected to the secondary supply lines downstream of the pumps. In this way, a time efficient cleaning process is performed.

When all the internal channels 24 are completely flushed with water, the cleaning process is essentially complete. However, as there is a contained water in the internal channels 24 of the endoscope, is advantageous to remove the water and minimise spillage once the endoscope is disconnected. For this reason, a further step of the cleaning process is the air purging step.

Figure 10:
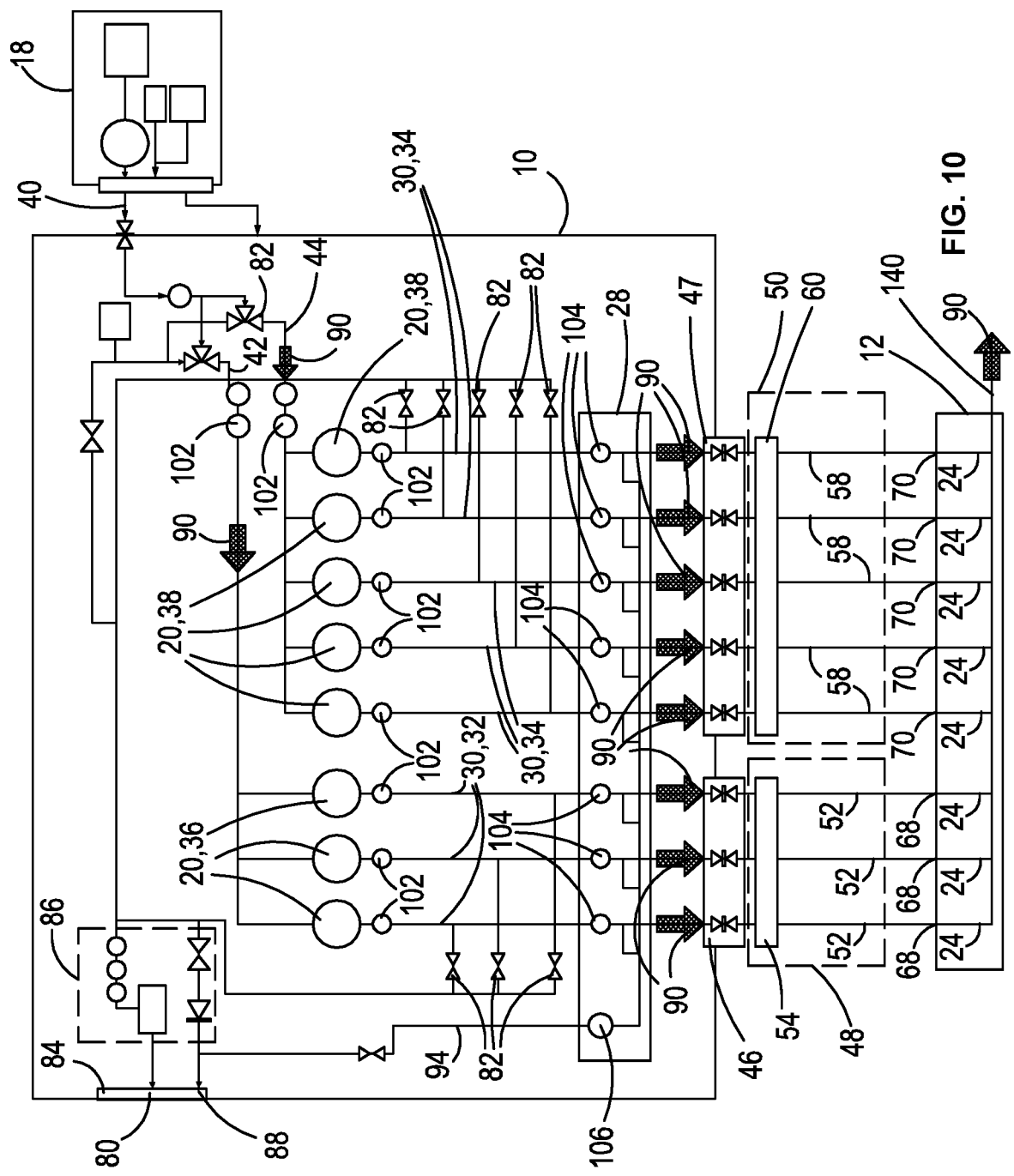
FIG. 10 is a schematic view of the cleaning apparatus of FIG. 1 depicting the inlets to each of the cleaning pumps being opened to atmosphere and the cleaning pumps pumping air to the medical device.

As shown in FIG. 10, in this step, the main feed line 40 is opened to atmosphere. Both the primary pumps 36 and secondary cleaning pumps 38 are then activated and begin pumping air 90 through the primary and secondary supply lines. Pumped air 90 is then passed through the primary and secondary transfer conduit assemblies and through each of the internal channels 24. In this way, the contained water within the internal channels is purged out of the endoscope.

When the air purging is complete, the display screen 16 will indicate to the user that the cleaning process is complete, and the primary and secondary endoscope connectors can be removed from the endoscope 12.

During the cleaning process, the presence of the viscoelastic liquid cleaning agent, water or air is confirmed using optical sensors 102. Moreover, any blockage of the viscoelastic liquid 22 during the process will be identified by the main logic control computer 100 which will read an excessive pressure from one of pressure sensors 104 and if necessary, the fluid will be released to atmosphere through the drain line 94 and its valve 108. Similarly, any loose or leaking connection between the endoscope connectors and endoscope, or coupling connectors and receivers the cleaning apparatus, will be identified by an insufficient pressure reading. Under either circumstance, the cleaning process will be paused, and a fault condition will be sent to the main display 16.

If during cleaning process, the primary endoscope connectors 56 becomes disconnected with the primary inlet apertures 68 on the endoscope 12, or the secondary endoscope connectors 62 with each of the secondary inlet apertures 70, a fault condition will be triggered. This disconnection is identified by monitoring the pressure in each of the primary or secondary supply lines during operation.

In one embodiment, the pressure of the supply line of the same port is monitored to identify the disconnection. In a further embodiment, the pressure of the supply lines of the other ports are monitored to identify this disconnection using a redundant pressure sensor 106 inside the drain line. Under these circumstances, the highest pressure of all the supply lines is monitored using the redundant pressure sensor 106 inside the drain line.

It should be appreciated that the cleaning apparatus of the present invention provides a means to efficiently and clinically clean the internal channels of a medical device and in particular, an endoscope. The degree of contamination within the medical device after cleaning has been found to meet all relevant standards and is substantially better than using prior art means.

The process is essentially automatic after initial setup, and its operation is very simple for an operator. Advantageously, the cleaning time has been optimised in order to minimise the down time of the medical device. The footprint of the cleaning apparatus 10 has also been optimised in order to minimise bench space usage.

It should be appreciated that in the above description of exemplary embodiments of the invention, various features of the invention are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

While there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A system for cleaning a medical device having one or more internal channels, said system including:
   a unit housing a viscoelastic liquid; and
   a cleaning apparatus fluidly connectable to said unit, said cleaning apparatus having at least one cleaning pump adapted to pump the viscoelastic liquid, wherein the at least one cleaning pump has individual flow control,
   wherein the at least one cleaning pump is fluidly connectable to said one or more internal channels such that said viscoelastic liquid can be pumped through each of said one or more internal channels at a controlled flow rate thereby removing contaminants from said one or more internal channels.

2. A system for cleaning a medical device according to claim 1, wherein said at least one cleaning pump is a peristaltic pump.

3. A system for cleaning a medical device according to claim 1, wherein the at least one cleaning pump comprises one or more primary cleaning pumps and one or more secondary cleaning pumps.

4. A system for cleaning a medical device according to claim 3, wherein said medical device includes larger internal channels and smaller internal channels, and wherein said one or more primary cleaning pumps are fluidly connectable to said larger internal channels and said one or more secondary cleaning pumps are fluidly connectable to said smaller internal channels.

5. A system for cleaning a medical device according to claim 1, wherein said at least one cleaning pump comprises one or more primary cleaning pumps and one or more secondary cleaning pumps, and wherein the system includes at least one primary feed line configured to receive said viscoelastic liquid and apportion said viscoelastic liquid among said one or more primary cleaning pumps and at least one secondary feed line configured to receive said viscoelastic liquid and apportion said viscoelastic liquid among said one or more secondary cleaning pumps.

6. A system for cleaning a medical device according to claim 1, further comprising a valve fluidly coupled to said at least one cleaning pump, to a supply of water, and to said viscoelastic liquid, wherein a first position of said valve directs water from said supply of water to said at least one cleaning pump, a second position of said valve directs said viscoelastic liquid to said at least one cleaning pump, and said valve is configured to selectably transition between said first position and said second position.

7. A system for cleaning a medical device according to claim 1, including a transfer conduit assembly which includes one or more conduits each being removably engageable with said at least one cleaning pump, wherein a pressure profile of said viscoelastic liquid flowing through said transfer conduit assembly while pumping said viscoelastic liquid is used to determine when said viscoelastic liquid has reached an entrance of said medical device.

8. A system for cleaning a medical device according to claim 1, wherein said unit includes a booster pump for pumping said viscoelastic liquid to said cleaning apparatus.

9. A system according to claim 1, wherein the at least one cleaning pump comprises a plurality of cleaning pumps, wherein each cleaning pump of said plurality of cleaning pumps is configured to direct a respective portion of said viscoelastic liquid to an individual internal channel of said one or more internal channels, and wherein each cleaning pump of said plurality of cleaning pumps is individually controllable to separately control flow of said respective portion of said viscoelastic liquid.

10. A method of cleaning one or more internal channels of a medical device using a cleaning apparatus having one or more cleaning pumps and a supply of viscoelastic liquid, each of the one or more cleaning pumps being fluidly connectable to said one or more internal channels, said method including said steps of:
(i) pumping said viscoelastic liquid through each of said one or more internal channels at a controlled flow rate to remove contaminants; and
(ii) rinsing each of said one or more internal channels with a flushing liquid.

11. A method according to claim 10 further including the step of purging said one or more internal channels with air.

12. A method according to claim 11, wherein presence of the viscoelastic liquid, flushing liquid or air is sensed using one or more optical sensors.

13. A method according to claim 12, including the step of measuring a flow rate of said viscoelastic liquid or flushing liquid using said one or more optical sensors associated with a logic control computer.

14. A method according to claim 10, wherein said controlled flow rate of the viscoelastic liquid is adjusted by a speed of at least one of the one or more cleaning pumps.

15. A method according to claim 10, wherein prior to step (i), said flushing liquid is heated to a preselected temperature.

16. A method according to claim 10, wherein said one or more internal channels include internal surfaces and said pumping said viscoelastic liquid through said one or more internal channels at said controlled flow rate removes contaminants from said internal surfaces.

17. A method according to claim 16, wherein said controlled flow rate induces a shear rate and/or strain on said internal surfaces thereby removing contaminants from said internal surfaces.

18. A system according to claim 9, comprising a plurality of supply lines, wherein each supply line of said plurality of supply lines is configured to receive said respective portion of said viscoelastic liquid from a respective cleaning pump of said plurality of cleaning pumps and direct said respective portion of said viscoelastic liquid to a respective internal channel of said one or more internal channels.

19. A method according to claim 10, including the step of flushing said one or more internal channels with a flushing liquid prior to step (i).

20. A system according to claim 18, wherein each supply line of said plurality of supply lines is connected to a respective water line configured to direct water from a supply of water.

* * * * *